(12) United States Patent
Reynaud et al.

(10) Patent No.: US 10,221,295 B2
(45) Date of Patent: Mar. 5, 2019

(54) RADIOOPAQUE PEEK BASED BLOCK FOR USE IN A CAD/CAM SYSTEM FOR THE MANUFACTURE OF A DENTAL RESTAURATION

(71) Applicants: SOCIETE DE RECHERCHES TECHNIQUES DENTAIRES—RTD, Saint Egreve (FR); SUKGYUNG AT CO., LTD, Ansan (KR)

(72) Inventors: Pierre-Luc Reynaud, Vaulnaveys le Haut (FR); Manh-Quynh Chu, Fontanil Cornillon (FR); Hyung Sup Lim, Ansan (KR); Hyung Jun Lim, Anyang (KR); Young Cheol Yoo, Ansan (KR)

(73) Assignees: SOCIETE DE RECHERCHES TECHNIQUES DENTAIRES—RTD, Saint Egreve (FR); SUKGYUNG AT CO., LTD, Ansan (KR)

( * ) Notice: Subject to any disclaimer, the term of this patent is extended or adjusted under 35 U.S.C. 154(b) by 0 days.

(21) Appl. No.: 15/561,998

(22) PCT Filed: Apr. 7, 2016

(86) PCT No.: PCT/EP2016/057631
§ 371 (c)(1),
(2) Date: Sep. 27, 2017

(87) PCT Pub. No.: WO2016/162427
PCT Pub. Date: Oct. 13, 2016

(65) Prior Publication Data
US 2018/0057656 A1    Mar. 1, 2018

(30) Foreign Application Priority Data

Apr. 7, 2015 (FR) ..................... 15 52949

(51) Int. Cl.
| | |
|---|---|
| *C08K 3/22* | (2006.01) |
| *A61L 27/44* | (2006.01) |
| *C08L 71/00* | (2006.01) |
| *C08K 3/11* | (2018.01) |
| *A61K 6/00* | (2006.01) |
| *A61K 6/087* | (2006.01) |

(52) U.S. Cl.
CPC ............... *C08K 3/22* (2013.01); *A61K 6/007* (2013.01); *A61K 6/0023* (2013.01); *A61K 6/0094* (2013.01); *A61K 6/087* (2013.01); *A61L 27/446* (2013.01); *C08K 3/11* (2018.01); *C08L 71/00* (2013.01); *A61L 2430/12* (2013.01); *C08G 2650/40* (2013.01)

(58) Field of Classification Search
CPC ...... C08K 3/22; A61K 6/0023; A61K 6/0094; A61K 6/007; A61K 6/087
USPC ........................................................ 428/384
See application file for complete search history.

(56) References Cited

U.S. PATENT DOCUMENTS

| | | | |
|---|---|---|---|
| 2006/0052479 A1 | 3/2006 | Cougoulic | |
| 2010/0035214 A1* | 2/2010 | Reynaud | A61C 13/30 433/220 |
| 2010/0099058 A1* | 4/2010 | Wang | A61C 13/0004 433/173 |
| 2011/0270407 A1* | 11/2011 | Cougoulic | A61K 6/033 623/23.61 |
| 2013/0323685 A1* | 12/2013 | Ostler | A61K 6/083 433/228.1 |

FOREIGN PATENT DOCUMENTS

| | | |
|---|---|---|
| WO | 96/03161 A1 | 2/1996 |
| WO | 2006/127838 A2 | 11/2006 |

OTHER PUBLICATIONS

PCT International Search Report and Written Opinion dated Jun. 28, 2016 from corresponding Application No. PCT/EP2016/057631, 13 pages.

* cited by examiner

*Primary Examiner* — Hui H Chin
(74) *Attorney, Agent, or Firm* — Dilworth IP, LLC

(57) ABSTRACT

Block for use in a CAD/CAM system for the manufacture of a dental restauration, said block consisting of a thermoplastic polymer comprising PEEK including radiopaque particles selected from the group comprising $BaZrO_3$, $YbF_3$, $Yb_2O_3$, SrO, $SrZrO_3$, $SiO_2$—$ZrO_2$, $SiO_2$—$Yb_2O_3$, $Lu_2O_3$, $LuF_3$.

18 Claims, No Drawings

RADIOOPAQUE PEEK BASED BLOCK FOR USE IN A CAD/CAM SYSTEM FOR THE MANUFACTURE OF A DENTAL RESTAURATION

The invention pertains to thermoplastic polymers materials used in particular in the field of dentistry. It more especially concerns a block consisting of a thermoplastic polymer for use in a CAD/CAM system for the manufacture of a dental restauration.

BACKGROUND OF THE INVENTION

Polymers such as PMMA, PE, or even PEEK are an ideal alternative as substitute materials of metallic or ceramic materials. Thus, they can be used for spinal, orthopedic or dental implants. They offer many advantages such as an absence of interferences with scanners, a biomechanical behavior similar to that of bone, a proved biocompatibility . . . . The preferred biocompatible polymer is PEEK (Polyether Ether Ketone), a thermoplastic polymer.

However, these polymers are unfortunately non radiopaque to X-rays. They are hardly detected when used in spinal, orthopedic or dental implants. Moreover, it is also difficult to detect their localisation when used in dental restorative materials, for instance, in case of accidental ingestion.

To the applicant's knowledge and to avoid this drawback, there is nowadays only one radiopaque PEEK polymer made with barium sulfate ($BaSO_4$) fillers. This compound is a white solid oxide, usually highly pure, used as an opacifier in paintings or as "boiled barium" in medical radiology, particularly for gastrointestinal tract monitoring.

Although such filled polymers have radio-opacity property, the radio opacity level remains quite low making them difficult to be detected, unless the fillers concentration is increased significantly. However, such concentration may cause final material having lower final mechanical properties. In addition, its high refractive index together with the large size of particles leads to a final product which is opaque to light or has a diminished aesthetic appearance. As already said, filled polymers have lower mechanical properties than unfilled polymers.

SUMMARY OF THE INVENTION

This present invention relates to a thermoplastic polymer selected from the group comprising PMMA, PE or PEEK including radiopaque particles selected from the group comprising BaO, $ZrO_2$, $BaZrO_3$, $YbF_3$, $Yb_2O_3$, SrO, $SrZrO_3$, $SiO_2$—$ZrO_2$, $SiO_2$—$Yb_2O_3$, $Lu_2O_3$, $LuF_3$.

Particles are incorporated into the polymer by grafting or incorporation methods. In practice, the polymer is formed as pellet-like.

DETAILED DESCRIPTION OF THE INVENTION

As above explained, metallic oxides, most particularly, heavy metals or rare earths compounds, barium sulfate, carbonates, are well-known to confer radiopaque properties to polymer-based composite materials. Particles are mixed together with the resin and the remainder material components during the manufacturing.

Preferred particles of the invention are selected from barium oxide (BaO), zirconium oxide ($ZrO_2$), barium zirconate ($BaZrO_3$), ytterbium fluorure ($YbF_3$), ytterbium oxide ($Yb_2O_3$) and a combination thereof for biocompatibility, implementation (dispersion, mechanical, optical (transparency), and cost reasons.

Radiopaque compounds consist of particles having preferably a spherical, rod-like or any other shapes. These particles may be functionnalised as well. Particles size is lower than 1 µm, preferably ranging from 0.2 to 0.9 µm.

In another embodiment, particles represent at least 2% by weight of total polymer weight.

MMA-based (Méthyl Méthacrylate) is the preferred component for functionalizing these particles due to its structure which makes easier its incorporation into PEEK.

Thus, radiopaque polymer formed can be used as medical implant material such as spinal, orthopedic, dental implants or dental block CAD CAM. It may also be used as polymeric matrix of a reinforced-fibers composite material in dental post, abutments applications . . . .

In an embodiment, the invention concerns a block for use in a CAD/CAM system for the manufacture of a dental restauration, said block consisting of a thermoplastic polymer comprising PEEK including radiopaque particles selected from the group comprising BaO, $ZrO_2$, $BaZrO_3$, $YbF_3$, $Yb_2O_3$, SrO, $SrZrO_3$, $SiO_2$—$ZrO_2$, $SiO_2$—$Yb_2O_3$, $Lu_2O_3$, $LuF_3$.

Advantageously, radiopaque particles are selected among $YbF_3$, $Yb_2O_3$ or $LuF_3$, $Lu_2O_3$.

The blocks of the invention are deprived of calcium and phosphates.

In some embodiments, the block contains pigments as coloring agent.

As dental restauration, the invention covers crowns, brides, abutments, bars . . . .

Many other embodiments may be possible for someone with ordinary skills in the art.

In practice, radiopaque polymer pellets are first ground and then cooled depending on the applications.

EXAMPLES

The goal of this example is to study the radiopacity of a block made of PEEK including $Yb_2O_3$ Material:
  Sample A: PEEK
  Sample B: PEEK 12% $Yb_2O_3$
  Sample C: PEEK 24% $Yb_2O_3$
Method:
  The method corresponds to that disclosed in ISO 4049.
  The sample are square having a length of around 5 mm and a thickness of 1±0.1 mm
  5 density measurements are made by sample. Measurements correspond to an equivalency of thickness of aluminium and then is divided by the thickness for obtaining the equivalency of 1 millimeter of material by aluminum millimeter.
  Sample A is not radiopaque. Samples B and C have a percentage aluminium equivalent of 113% and 303% and are both radiopaque.

The invention claimed is:
1. A block for use in a CAD/CAM system for the manufacture of a dental restoration, which dental restoration is a crown, bridge, abutment or bar, said block consisting of a thermoplastic polymer comprising PEEK including radiopaque particles, wherein said particles are selected from the group consisting of $BaZrO_3$, $YbF_3$, $Yb_2O_3$, $SrZrO_3$, $SiO_2$—$ZrO_2$, $SiO_2$—$Yb_2O_3$, $Lu_2O_3$ and $LuF_3$.

2. The block according to claim 1, wherein radiopaque particles are selected from the group consisting of $YbF_3$ and $Yb_2O_3$.

3. The block according to claim 1, wherein radiopaque particles are particles of $LuF_3$.

4. The block according to claim 1, wherein the radiopaque particles have a particle size lower than 1 μm.

5. The block according to claim 4, wherein the radiopaque particles have a particle size of from 0.2 μm to 0.9 μm.

6. The block according to claim 2, wherein the radiopaque particles have a particle size lower than 1 μm.

7. The block according to claim 6, wherein the radiopaque particles have a particle size of from 0.2 μm to 0.9 μm.

8. The block according to claim 3, wherein the radiopaque particles have a particle size lower than 1 μm.

9. The block according to claim 8, wherein the radiopaque particles have a particle size of from 0.2 μm to 0.9 μm.

10. The block according to claim 1, wherein particles represent at least 2% by weight of total polymer weight.

11. The block according to claim 2, wherein particles represent at least 2% by weight of total polymer weight.

12. The block according to claim 3, wherein particles represent at least 2% by weight of total polymer weight.

13. The block according to claim 4, wherein particles represent at least 2% by weight of total polymer weight.

14. The block according to claim 6, wherein particles represent at least 2% by weight of total polymer weight.

15. The block according to claim 8, wherein particles represent at least 2% by weight of total polymer weight.

16. The block according to claim 1, wherein said polymer is pellet like in the form of a pellet.

17. A block for use in a CAD/CAM system for the manufacture of a dental restoration, which dental restoration is a crown, bridge, abutment or bar, said block consisting of a thermoplastic polymer comprising PEEK including radiopaque particles, wherein said particles are selected from the group consisting of $BaZrO_3$, $YbF_3$, $Yb_2O_3$, $SrZrO_3$, $SiO_2$—$ZrO_2$, $SiO_2$—$Yb_2O_3$, $Lu_2O_3$ and $LuF_3$, and one or more pigments.

18. The block according to claim 1, wherein the dental restoration is a crown, abutment, or bar.

* * * * *